US009566224B2

(12) United States Patent
Hu et al.

(10) Patent No.: US 9,566,224 B2
(45) Date of Patent: Feb. 14, 2017

(54) TYROSINASE INHIBITORS

(71) Applicant: Avon Products, Inc., New York, NY (US)

(72) Inventors: Hong Hu, Basking Ridge, NJ (US); Sunghan Yim, Lincoln Park, NJ (US); Uma Santhanam, Tenafly, NJ (US); John W. Lyga, Basking Ridge, NJ (US)

(73) Assignee: AVON PRODUCTS, INC., New York, NY (US)

( * ) Notice: Subject to any disclaimer, the term of this patent is extended or adjusted under 35 U.S.C. 154(b) by 0 days.

(21) Appl. No.: 14/586,883

(22) Filed: Dec. 30, 2014

(65) Prior Publication Data
US 2015/0118170 A1  Apr. 30, 2015

Related U.S. Application Data

(63) Continuation of application No. PCT/US2014/021187, filed on Mar. 6, 2014.

(60) Provisional application No. 61/779,263, filed on Mar. 13, 2013.

(51) Int. Cl.
| A61K 8/49 | (2006.01) |
| A61Q 19/02 | (2006.01) |
| A61Q 19/08 | (2006.01) |
| A61Q 19/00 | (2006.01) |
| A61K 31/17 | (2006.01) |
| A61K 31/175 | (2006.01) |

(52) U.S. Cl.
CPC ........... *A61K 8/4973* (2013.01); *A61K 8/49* (2013.01); *A61K 31/175* (2013.01); *A61Q 19/00* (2013.01); *A61Q 19/007* (2013.01); *A61Q 19/02* (2013.01); *A61Q 19/08* (2013.01); *A61K 2800/10* (2013.01); *A61K 2800/40* (2013.01)

(58) Field of Classification Search
CPC ............ A61K 2800/10; A61K 2800/40; A61K 31/175; A61K 8/49; A61K 8/4973; A61K 8/00; A61Q 19/00; A61Q 19/007; A61Q 19/02; A61Q 19/08
See application file for complete search history.

(56) References Cited

U.S. PATENT DOCUMENTS

| 4,064,261 A | 12/1977 | Paget |
| 4,310,551 A | 1/1982 | Gullo et al. |
| 4,477,662 A | 10/1984 | Corbett et al. |
| 5,086,052 A | 2/1992 | Brooks et al. |
| 5,976,555 A | 11/1999 | Liu et al. |
| 7,700,076 B2 | 4/2010 | Tamarkin et al. |
| 8,920,785 B2 | 12/2014 | Kolbe et al. |
| 2003/0125325 A1 | 7/2003 | Heinemann et al. |
| 2007/0037785 A1 | 2/2007 | Ansorge et al. |
| 2008/0312255 A1 | 12/2008 | Basarab et al. |
| 2009/0023793 A1 | 1/2009 | Dooley et al. |
| 2010/0286102 A1 | 11/2010 | Vielhaber |
| 2010/0298562 A1 | 11/2010 | Dubreuil et al. |
| 2013/0039870 A1 | 2/2013 | Kolbe et al. |

FOREIGN PATENT DOCUMENTS

| DE | 4207400 A1 * | 9/1993 | ............. A01N 47/24 |
| EP | 0128502 A1 | 12/1984 | |
| KR | 10-2011-0097701 A | 8/2011 | |
| KR | 20110097701 A * | 8/2011 | |
| WO | 2006103119 A2 | 10/2006 | |
| WO | 2008051808 A2 | 5/2008 | |
| WO | 20110117034 A2 | 9/2011 | |
| WO | 20130076633 A1 | 1/2013 | |

OTHER PUBLICATIONS

Thanigaimalai et al (Biorganic and Medicinal Chemistry Letters, online Dec. 13, 2011, vol. 22, pp. 886-889).*
DE4207400 A1, Espacenet English translation of description, acquired on Jun. 17, 2016.*
Commonwealth of Pennsylvania, The Controlled Substances, Drugs, Device, and Cosmetic Act. of 1972, P.O. 233, No. 64, pp. 1-32 [online], (retrieved on May 6, 2014]. Retrieved from the Internet <URL: http://www.health.state.pa.us/pdf/ddc/ddcAct.pdf>; p. 3, paragraph 16; p. 4, paragraph 12.
Dehaven, C. Causes of Skin Aging, Science of Skincare, LLC, 2007, pp. 1-4 [online], [retrieved on May 6, 2014] Retrieved from the Internet <URL: http://www.isclinical.com/whitepapers/skin-aging.pdf>; p. 1, paragraph 8.
Gao, Xing-Hua et al., "Efficacy and safety of innovative cosmeceuticals," Clinics in Dermatology, vol. 26, pp. 367-374 (2008).
Parvez, Shoukat et al., "Naurally Occurring Tyrosinase Inhibitors: Mechanism and Applications in Skin Health, Cosmetics and Agriculture Industries," Phytotherapy Research, vol. 21, pp. 805-816 (2007).
Pubchem. CID 20202112. Dec. 5, 2007, pp. 1-4 [online], [retrieved on May 6, 2014], Retrieved from the Internet <URL: http://pubchem.ncbi.nlm.nih.gov/summary/summary.cgi?cid=2-2-2112>; p. 1, formula, 4,5-Dihydro-6-(5-(2-(pyrrolidin-1-yl)-ethyl)-thien-2-yl)-3(2H)-pyridazinone.
Pubchem. CID 3037083. Aug. 9, 2005, pp. 1-3 [online], [retrieved on May 6, 2014]. Retrieved from the Internet <URL: http://pubchem.ncbi.nlm.nih.gov/summary/summary.cgi? cid=3037083 &loc=ec_rcs>; p. 1, formula, 5-phenyl-as-triazine-3-thiol.

(Continued)

*Primary Examiner* — Mark V Stevens
(74) *Attorney, Agent, or Firm* — Jonathan D. Ball; Greenberg Traurig LLP

(57) ABSTRACT

The compositions and methods of described herein comprise novel ingredients effective to reduce unwanted pigmentation, such as skin discoloration, freckles, age spots, liver spots, sun damage, tans, pigmented acne marks, scars, pigmented birthmarks, hyperpigmentation, post-inflammatory hyperpigmentation, post-injury hyperpigmentation, melasma, cholasma, after-burn scar, nail stain, yellowing of skin, dark circles under eyes, and the like. The composition may include additional ingredients accordingly for a colored cosmetic, moisturizer, cleanser, toner, and the like.

8 Claims, No Drawings

(56) References Cited

OTHER PUBLICATIONS

Pubchem. CID 16227230. Jul. 30, 2007, pp. 1-3 [online], [retrieved on May 6, 2014]. Retrieved from the Internet <URL:http://pubchem.ncbi.nlm.nih.gov/summary/sunimary.cgi? cid=16227230 &loc=ec_rcs>: p. 1, formula, 643,5-dimethyl-1H-pyrazol-1-yl)pyridazine-3-thiol.

Pubchem. CID 7131297. Jul. 29, 2007, pp. 1-3 [online],[retrieved on May 6, 2014]. Retrieved from the Internet <URL: http://pubchem.ncbi.nlm.nih.gov/summary/summary.cgi? cid=7131297 &loc=ec_rcs>; p. 1, formula, 5-isopropyl-phenyl-1H-1,2,4-triazole-3-thiol.

Pubchem. CID 703960. Jul. 8, 2007, pp. 1-3 [online], [retrieved on May 6, 2014]. Retrieved from the Internet <URL: http://pubchem.ncbi.nlin.nih.gov/summary/summary.egi? i:id=7039608doc=ec_rcs>: p. 1, formula, 9-methyl-2-,9-dihydro-3H[1,2,4]triazolo[4,3-a]benzimidazole-3-thione.

Pubchem. BRN 0146267. Aug. 9, 2005; pp. 1-3 [online], [retrieved on May 6, 2014]. Retrieved from the Internet <URL:http://pubchem.ncbi.nlm.nih.gov/summary/summary.cgi?cid=3062525 &loc=ec_rcs>; p. 1, formula, 5-thien-2-yl-1,2,4-triazine-3(2H)-thione.

* cited by examiner

TYROSINASE INHIBITORS

CROSS-REFERENCE TO RELATED APPLICATION

This patent application claims priority to International Application No. PCT/US2014/021187, filed Mar. 6, 2014, which claims the benefit to U.S. Patent Application Ser. No. 61/779,263, filed on Mar. 13, 2013. The entirety of both applications are incorporated herein in their entirety by reference.

FIELD OF INVENTION

The present invention relates generally to novel compounds, cosmetic formulations, and methods of improving the aesthetic appearance and health of human skin. In particular, the invention relates to substances that reduce unwanted pigmentation in human skin.

BACKGROUND

Several skin conditions are associated with the overproduction or unwanted production of melanin the skin, including age spots, freckles, and liver spots. The synthesis of melanin occurs in melanocyte cells in the skin and is a complex process involving several biochemical pathways. Some skin lighteners or depigmenting agents act as inhibitors of tyrosinase, an enzyme that has its catalytically active domain within organelles known as melanosomes. Tyrosinase converts phenols such as tyrosine to ortho-quinones which are subsequently converted to melanin within the melanosomes. Other skin lighteners act by disrupting the transfer of the melanosomes from melanocytes to the keratinocytes where melanin is deposited.

While these lightening agents do work, they may exhibit in some individuals having sensitivity thereto certain side effects. Some of the side effects of lightening agents include, but are not limited to: redness, itching, stinging, burning, crusting, swelling, unusual discoloration.

Therefore, there is a continuing need for products that effectively whiten or lighten or otherwise reduce pigmentation of skin. In particular, it treatment of skin that has hyperpigmentation such as age spots, liver spots, sun spots, freckles, scars, and the like. In particular, there is a need for depigmenting products that overcome one or more disadvantages of the prior art, including improved effectiveness, and reduced irritation and side effects.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application. The foregoing discussion is presented solely to provide a better understanding of nature of the problems confronting the art and should not be construed in any way as an admission as to prior art.

SUMMARY OF THE INVENTION

In accordance with the foregoing objectives and others, the present invention provides compounds and cosmetic formulations thereof that improve one or more signs of dermatological aging and/or skin depigmentation when topically applied to human integuments (skin, lips, nails, hair, etc.), particularly skin. The invention ideally provides compositions and methods for reducing unwanted pigmentation in human skin. The compositions and methods may treat hyperpigmentation conditions, including those associated with UV damage and chronological aging, including without limitation treating, ameliorating, diminishing the appearance of, or preventing age spots, liver spots, freckles, and the like. The compositions and methods are also useful for reducing otherwise unwanted pigmentation, including overall lightening of the skin.

In one aspect of the invention, cosmetic compositions are provided for improving the aesthetic appearance of human skin comprising a cosmetically acceptable vehicle, and an effective amount of a diazothione active agent that reduces pigmentation in keratinous biological substrates, including the skin. The cosmetic composition may comprise a compound according to formula I(a):

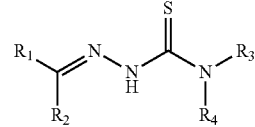

I(a)

wherein, $R_1$ and $R_2$ are independently selected from hydrogen, aliphatic $C_1$-$C_{12}$ hydrocarbon radicals; aromatic $C_1$-$C_{12}$ hydrocarbon radicals; aliphatic $C_1$-$C_{12}$ heterocycles, aromatic $C_1$-$C_{12}$ heterocycles, or combinations thereof; each of the foregoing optionally containing from 1-8 heteroatoms selected from halogen, O, N, and S and being optionally substituted with one or more groups R, and wherein $R_1$ and $R_2$ may together form a three- to six-membered ring, with the proviso that one of $R_1$ and $R_2$ are not hydrogen;

$R_3$ and $R_4$ are independently selected from hydrogen, aliphatic $C_1$-$C_{12}$ hydrocarbon radicals; aromatic $C_1$-$C_{12}$ hydrocarbon radicals; aliphatic $C_1$-$C_{12}$ heterocycles, aromatic $C_1$-$C_{12}$ heterocycles, or combinations thereof; each of the foregoing optionally containing from 1-8 heteroatoms selected from halogen, O, N, and S and being optionally substituted with one or more groups R, and wherein $R_3$ and $R_4$ may together form a three- to six-membered heterocyclic ring, with the proviso that one of $R_3$ and $R_4$ are not hydrogen;

R is selected, independently at each occurrence, from hydrogen, —F; —Cl; —Br; —I; =O, —OH, —OR*; —NH$_2$; —NHR*; —N(R*)$_2$; —N(R*)$_3^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)—N(R*)$_2$; —SH; —SR*; —CN; —NC; —(C=O)—R*; —CHO; —CO$_2$H; —CO$_2^-$; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —(C=NR)—O—R*; —O—(C=NR*)—R*, —SCN; —NCS; —NSO; —SSR*; —N(R*)—C(=O)—N(R*)$_2$; —N(R*)—C(=S)—N(R*)$_2$; —SO$_2$—R*; —O—S(=O)$_2$—R*; —S(=O)$_2$—OR*; —N(R*)—SO$_2$—R*; —SO$_2$—N(R*)$_2$; —O—SO$_3^-$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; $C_1$-$C_8$ perfluoroalkyl; an aliphatic $C_1$-$C_8$ hydrocarbon radical; a $C_1$-$C_8$ aromatic hydrocarbon radical; or a $C_1$-$C_8$ heteroaryl radical;

where R* is independently at each occurrence hydrogen or a straight chained, branched, or cyclic $C_1$-$C_{20}$ hydrocarbon radical, which may be saturated, partially saturated, or aromatic, each of which may be optionally substituted with one or more groups R, or optionally substituted with 1-6 heteroatoms selected from nitrogen, oxygen, sulfur, or halogen; and cosmetically acceptable salts thereof.

In a related aspect, the compound may have a structure according to Formula I(b):

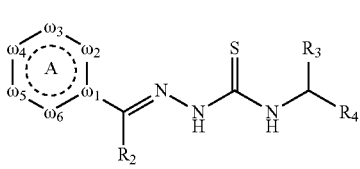

I(b)

where ring "A" is a five or six-membered optionally aromatic ring, $\omega_1$ is C or N; and $\omega_2$-$\omega_6$ are independently selected from —N—, —NH—, —NR*—, —NL$_1$-, —O—, —S—, —CH—, —CR—, —CR*—, and —CL$_1$-, in the case where ring "A" is a five membered ring, $\omega_4$ is a bond (i.e., it is absent); and wherein $\omega_2$ or $\omega_6$ may also be a group —NL$_1$- or —CL$_1$-, where L$_1$ is a linking moiety that forms a linkage between ring A and R$_2$, where L$_1$ is group —X$^a$—(CH$_2$)$_n$—(CH═CH)$_m$—X$^b$—(CH$_2$)$_n$—(CH═CH)$_m$—X$^c$—, where X$^a$, X$^b$, and X$^c$ are independently a bond (i.e., absent), —O—, —S—, —NH—, —NR*— and "n" and "m" are independently at each occurrence integers from 0-2, with the proviso that L$_1$ comprises no more than four atoms in the direct chain between rings A and R$_2$;

Exemplary compounds according to this aspect of the invention include, without limitation, the following:

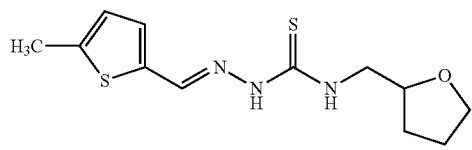

AV3793

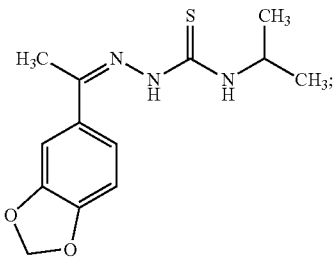

AV2043

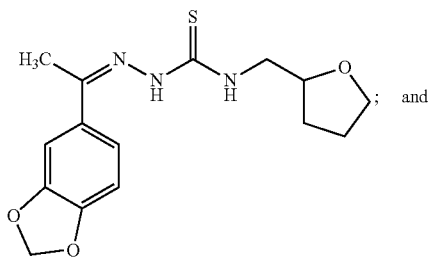

AV1221

; and

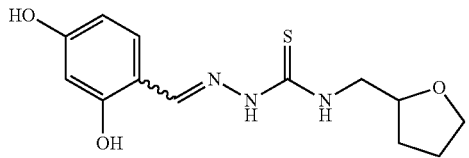

AV6989 and cosmetically acceptable salts thereof.

In a related aspect, cosmetic compositions are provided for improving the aesthetic appearance of human skin comprising a cosmetically acceptable vehicle, and an effective amount of a diazothioether active agent that reduces pigmentation in keratinous biological substrates, including the skin. The cosmetic composition may comprise a compound according to formula II(a):

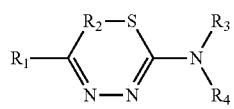

II(a)

wherein, R$_2$ is either a bond (i.e., it is absent) or a methylene group —CH$_2$—; and R$_1$, R$_3$, R$_4$, R and R* are as defined above; and cosmetically acceptable salts thereof. An exemplary compound according to formula II(b) has the structure:

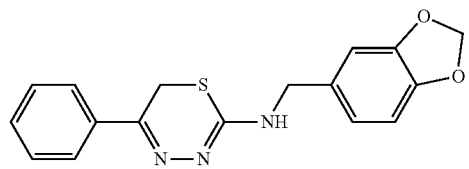 [SMILES: c1ccc(C2=NN=C(NCc3ccc4c(c3)OCO4)SC2)cc1]

The compositions of the invention will typically include a cosmetically or dermatologically acceptable vehicle, which may be in the form of, for example, a serum, a cream, a lotion, a gel, or a stick, and may comprise an emulsion (e.g., water-in-oil, oil-in-water, water-in-silicone, silicone-in-water, polyol-in-silicone, silicone-in-polyol emulsion, etc.), or may comprise an aqueous or ethanolic vehicle, silicone (e.g., cyclomethicone, dimethicone, etc.), hydrocarbon (e.g., petrolatum, isododecane, etc.), ester oil (isopropyl myristate, myristyl myristate, or the like. The vehicle may further comprise an emulsifier, gelling agent, structuring agent, rheology modifier (e.g., a thickener), film former, or the like. The compositions of the invention may optionally include additional skin benefit agents such as emollients (dimethicone oils, ester oils, or hydrocarbon oils), humectants (e.g., polyols, including propylene glycol, glycerin, etc.), antioxidants (e.g., BHT, ascorbic acid, sodium ascorbate, ascorbyl palmitate, beta-carotene, etc.), vitamins (e.g., tocopherol, tocopheryl acetate, etc.), alpha-hydroxy acids (e.g., glycolic acid), beta-hydroxy acids (e.g., salicylic acid), retinoids (e.g., retinoic acid, all-trans-retinoic acid, retinaldehyde, retinol, and retinyl esters such as acetates or palmitates), other anti-aging ingredients (e.g., collagen stimulators), as well as additional depigmenting agents (e.g., kojic acid, TDPA, Niacinamide, etc.).

It is a further object of the present disclosure to provide methods comprising topically applying such depigmenting compositions to skin. The composition may be applied once or twice daily, or more frequently, and the treatment regimen may last for as long as required to obtain the desired visible reduction in pigmentation, which may be, for example, one week, four weeks, eight weeks, twelve weeks or longer. The compositions may be applied to human keratinous surfaces, such as skin, to treat, ameliorate, diminish, or prevent, or delay the onset of one or more of dark complexion, pigmented skin discoloration, pigmented birthmarks, hyperpigmentation, post-inflammatory hyperpigmentation, post-injury hyperpigmentation, freckles, age spots, liver spots, sun damage, tans, pigmented acne marks, scars, melasma, cholasma, after-burn scars, nail stains, yellowing of skin, or dark circles under eye.

Further aspects, features and advantages of the present invention will be better appreciated upon a reading of the following detailed description of the invention and claims.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Therefore, specific structural and functional details disclosed herein are not to be interpreted as limiting, but merely as a representative basis for teaching one skilled in the art to variously employ the present invention.

All terms used herein are intended to have their ordinary meaning unless otherwise provided. By "cosmetically acceptable," it is meant that a particular component is generally regarding as safe and non-toxic at the levels employed. The term "prevent," as used herein, includes delaying the onset of or progression of a particular sign of skin aging. The term "thin skin" includes skin that becomes thinner with chronological aging as well as prematurely thinned skin, which may be caused, for example, by photoaging. In one embodiment, the prematurely thinned skin has been diagnosed as such by a clinician. The phrase "individual in need thereof" refers to a human that could benefit from improved dermal appearance or health, including males or females. In some embodiments, the individual in need thereof is a female. The term "skin" includes, without limitation, the lips, skin of the face, hands, arms, neck, scalp, and chest. As used herein, the term "consisting essentially of" is intended to limit the invention to the specified materials or steps and those that do not materially affect the basic and novel characteristics of the claimed invention, as understood from a reading of this specification.

The invention provides compositions for reducing pigmentation and/or lightening areas of the integumentary system, including but not limited to, skin, hair, lips, and nails. The compositions are, in one embodiment, topical compositions that once applied to the biological substrate result in a lightening of the biological substrate. As used herein, "skin" refers to the biological substrate of the integumentary system that includes skin, hair, lips, nails, and the like.

In some embodiments, the composition and methods are for the treatment of hyperpigmentation, which includes reducing, ameliorating, or reversing a degree of subject pigmentation that results from increased presence of one or more of the different types of melanin biosynthesized in skin and/or follicles and deposited in hair or skin, relative to a subject's baseline pigmentation.

In some embodiments, the composition and methods are for lightening skin, which includes reducing, ameliorating, and/or reversing a baseline degree of subject pigmentation. Lightening skin may be measured by observing changes in Fitzpatrick scale value of a subject. The Fitzpatrick Scale (aka, Fitzpatrick skin typing test or Fitzpatrick phototyping scale) is a numerical classification schema for the color of skin, and remains a recognized tool for dermatologic research into the color of skin. The Fitzpatrick Scale measures several components, including Genetic Disposition, Reaction to Sun Exposure and Tanning Habits., and classifies skin into six types: Type I (scores 0-7) refers to white, very fair skin, freckles, typical albino skin, that always burns, never tans; Type II (scores 8-16) refers to white, fair skin, that usually burns, or tans with difficulty; Type III (scores 17-24) refers to beige, which is very common, and which sometimes suffers mild burn, gradually tans to a light brown; Type IV (scores 25-30) refers to beige skin with a brown tint, which is typical of Mediterranean Caucasian skin, and which rarely burns, tans with ease to a moderate brown; Type V (scores over 30) refers to dark brown skin which very rarely burns, tans very easily; Type VI refers to Black skin that never burns, tans very easily, and is deeply pigmented. In some embodiments of the invention, the treatments are capable of changing the treated area of skin by at least one or at least two skin type on the Fitzpatrick scale.

It is to be understood that, as used herein, the terms treating and treatment include and encompass reducing, ameliorating, improving, and/or alleviating the dermatological effects of aging and/or environmental stress, or otherwise reducing the appearance of pigmentation in the skin. The present compositions and methods are suitable for use in treating dermatological conditions of the skin in numerous areas of the body, including, without limitation, the face, forehead, lips, neck, arms, hands, legs, knees, feet, chest, back, groin, buttocks, thighs, and the like. In one embodiment, the compositions are applied to the face, chest, and/or hands.

Specific benefits which may be achieved include, but are not limited to, reducing pigmentation of dark or hyperpigmented skin; reducing age spots or liver spots; reducing pigmented birthmarks, sun damage, tans, pigmented acne marks, scars; evening out or optimizing skin discoloration; decreasing the appearance of dark circles under the eyes; treating melasma, cholasma, freckles, after-burn scars, yellowing of skin, and post-injury hyperpigmentation; lightening hair on the scalp, legs, face, and other areas where whitening and color reduction are desired; and removing or reducing nail stains.

The present composition and methods of use thereof are not limited by any particular characterization of the physiological and/or chemical effects of lightening agents. Various skin lightening pathways are known and include, for example, those that occur by decreasing melanogenesis by decreasing tyrosinase activity in melanocytes as well as inhibiting melanosome maturation. However, the lightening agents used in the present compositions and methods are believed to lighten by multiple modes of action and by inhibiting the transfer of melanin from the melanocytes to the keratinocytes.

The cosmetic compositions of the invention may comprise a compound according to formula I(a):

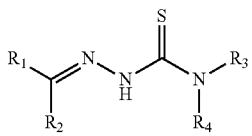

I(a)

Typically, $R_1$ and $R_2$ are independently selected from hydrogen, aliphatic $C_1$-$C_{12}$ (or $C_1$-$C_6$) hydrocarbon radicals (e.g., alkyl, alkenyl, alkynyl, etc.); aromatic $C_1$-$C_{12}$ (or $C_{1\text{-}8}$) hydrocarbon radicals (e.g., phenyl, toluyl, etc.); aliphatic $C_1$-$C_{12}$ (or $C_{1\text{-}8}$) heterocycles (e.g., tetrahydrofuryl), aromatic $C_1$-$C_{12}$ (or $C_{1\text{-}8}$) heterocycles (e.g., thiophen, imidazole, etc.), or combinations thereof. Each of these radicals may optionally containing from 1-8 (or from 1-6 or from 1-4 or from 1-3) heteroatoms selected from halogen, O, N, and S (i.e., pendent from the main chain (e.g., oxa) or as part of the main chain (e.g., oxo)) and being optionally substituted with one or more groups R. In some embodiments, $R_1$ and $R_2$ may together form a three- to six-membered ring. In some embodiments, one of $R_1$ and $R_2$ are not hydrogen. In some embodiments, both of $R_1$ and $R_2$ are not hydrogen.

$R_3$ and $R_4$ are independently selected from hydrogen, aliphatic $C_1$-$C_{12}$ hydrocarbon radicals; aromatic $C_1$-$C_{12}$ hydrocarbon radicals; aliphatic $C_1$-$C_{12}$ heterocycles, aromatic $C_1$-$C_{12}$ heterocycles, or combinations thereof; each of the foregoing optionally containing from 1-8 (or from 1-6 or from 1-4 or from 1-3) heteroatoms selected from halogen, O, N, and S and being optionally substituted with one or more groups R, and wherein $R_3$ and $R_4$ may together form a three- to six-membered heterocyclic ring, with the proviso that one of $R_3$ and $R_4$ are not hydrogen;

R is selected, independently at each occurrence, from hydrogen, —F; —Cl; —Br; —I; =O, —OH, —OR*; —NH$_2$; —NHR*; —N(R*)$_2$; —N(R*)$_3^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)—N(R*)$_2$; —SH; —SR*; —CN; —NC; —(C=O)—R*; —CHO; —CO$_2$H; —CO$_2^-$; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —(C=NR) O—R*; —O—(C=NR*)—R*, —SCN; —NCS; —NSO; —SSR*; —N(R*)—C(=O)—N(R*)$_2$; —N(R*)—C(=S)—N(R*)$_2$; —SO$_2$—R*; —O—S(=O)$_2$—R*; —S(=O)$_2$—OR*; —N(R*)—SO$_2$—R*; —SO$_2$—N(R*)$_2$; —O—SO$_3^-$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; $C_1$-$C_8$ perfluoroalkyl; an aliphatic $C_1$-$C_8$ hydrocarbon radical; a $C_1$-$C_8$ aromatic hydrocarbon radical; or a $C_1$-$C_8$ heteroaryl radical;

where R* is independently at each occurrence hydrogen or a straight chained, branched, or cyclic $C_1$-$C_{20}$ or $C_1$-$C_{16}$ or $C_1$-$C_{12}$ or $C_1$-$C_8$ or $C_1$-$C_6$ hydrocarbon radical, including lower alkyl radicals (e.g., methyl, ethyl, propyl, isopropyl, n-butyl, tert-butyl, iso-butyl, etc.) which may be saturated, partially saturated, or aromatic, each of which may be optionally substituted with one or more (e.g., one, two, three, four or more) groups R, or optionally substituted with 1-6 (or from 1-4 or from 1-3 or from 1-2) heteroatoms selected from nitrogen, oxygen, sulfur, or halogen (e.g., fluoro, chloro, bromo, iodo); and cosmetically acceptable salts thereof.

Where $R_1$ is a cyclic moiety, the compound may have a structure according to Formula I(b):

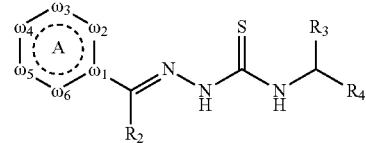

I(b)

where ring "A" is a five or six-membered optionally aromatic ring (or containing zero, one, two, or three double bonds), $\omega_1$ is C or N; and $\omega_2$-$\omega_6$ are independently selected from —N—, —NH—, —NR*—, —O—, —S—, —CH—, —CR—, —CR*—. In the case where ring "A" is a five membered ring, $\omega_4$ is a bond (i.e., it is absent). In some embodiments, $\omega_2$ or $\omega_6$ may also be a group —NL$_1$- or —CL$_1$-, where L$_1$ is a linking moiety that forms a linkage between ring A and $R_2$, where L$_1$ is group —X$^a$—(CH$_2$)$_n$—(CH=CH)$_m$—X$^b$—(CH$_2$)$_n$—(CH=CH)$_m$—X$^c$—, where X$^a$, X$^b$, and X$^c$ are independently a bond (i.e., absent), —O—, —S—, —NH—, —NR*— and "n" and "m" are independently at each occurrence integers from 0-2, with the proviso that L$_1$ comprises no more than four (e.g., one, two, three, or four) atoms in the direct chain between rings A and $R_2$.

In one embodiment, wherein $\omega_4$ is a bond (i.e., it is absent), ring "A" may be selected from the group consisting of:

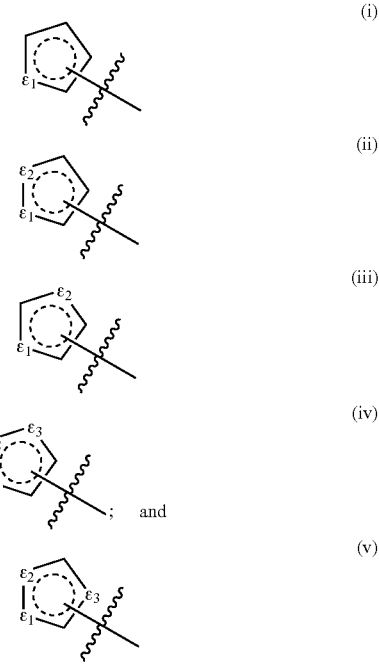

wherein $\epsilon_1$, $\epsilon_2$, and $\epsilon_3$, are independently selected from N, NH, NR*, S, and O; with the proviso that where the point of attachment is $\epsilon_1$, $\epsilon_2$, or $\epsilon_3$, then that position represents N; and wherein carbon atoms which are not the point of attachment may be optionally substituted with a group R; and wherein the dashed circles indicate that each ring may comprise zero, one, or two double bonds. In some embodiments, ring "A" is a ring Q having the form:
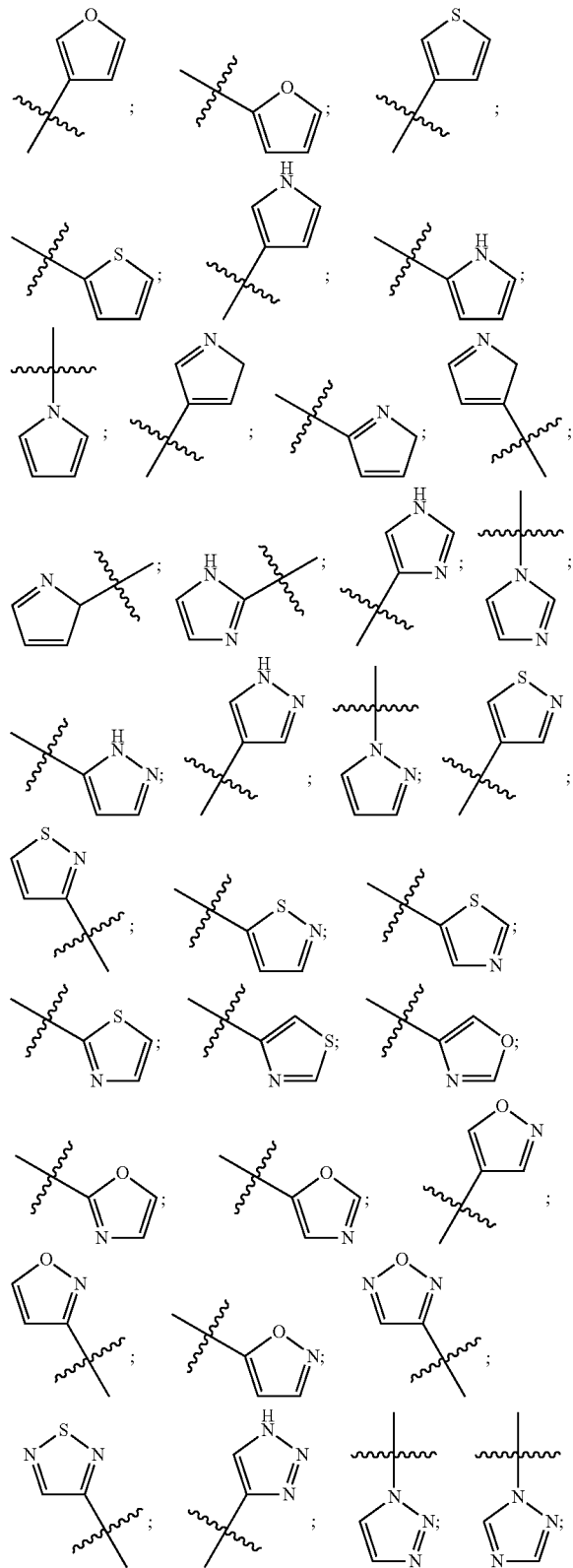
-continued
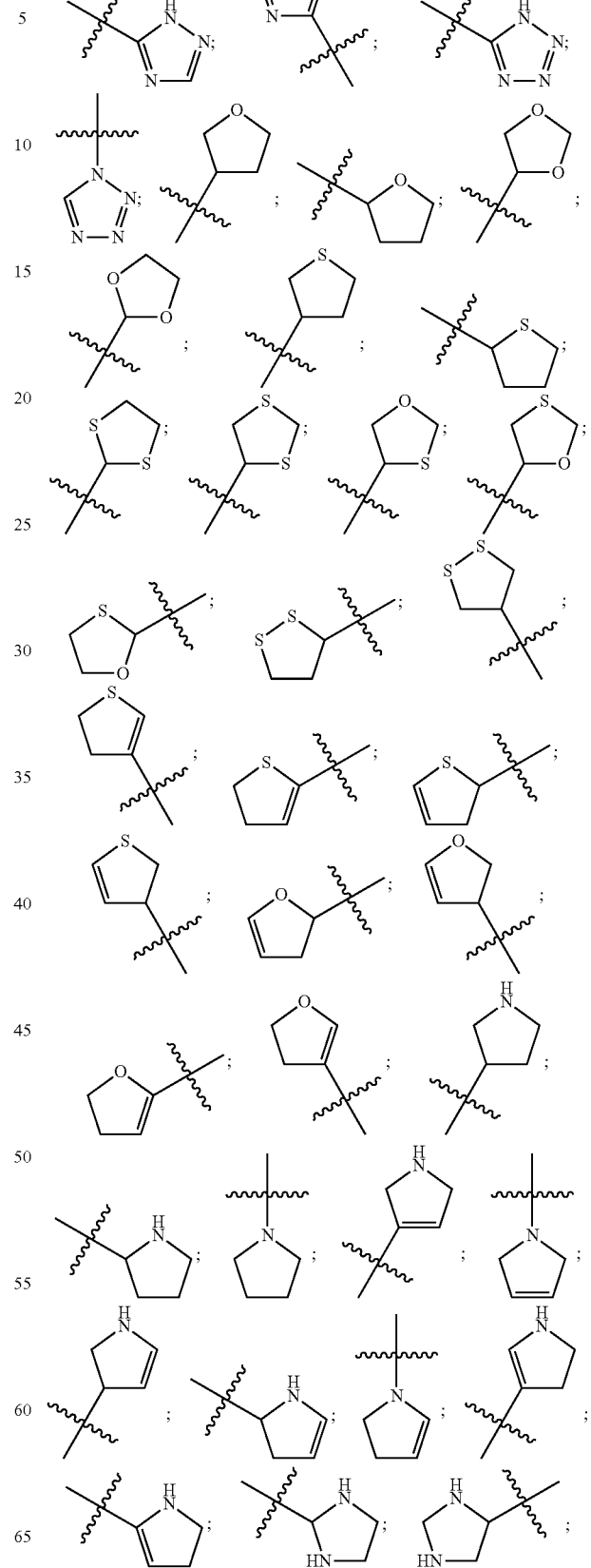

-continued

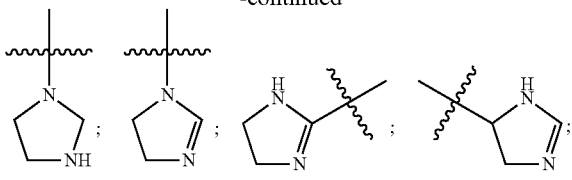

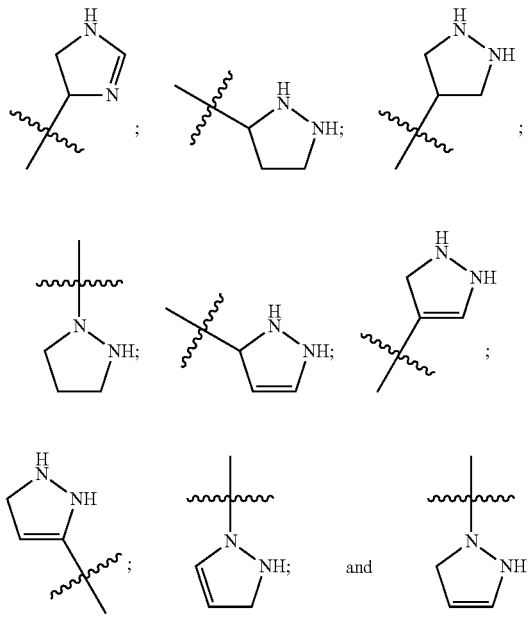

wherein any available site on the ring "A" or "Q" may be optionally substituted with a group R (e.g., methyl, methoxy, halo, hydroxyl, amino, etc.). In some embodiments, ring "A" is:

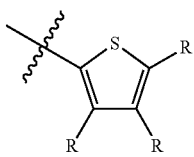

where R is independently at each occurrence hydrogen or lower alkyl (e.g., methyl, ethyl, isopropyl, etc.), including, without limitation the following:

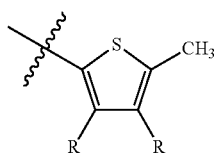

where R is independently at each occurrence hydrogen or lower alkyl and in one embodiment R is hydrogen at one occurrence, and in another embodiment, R is hydrogen at both occurrences.

In another embodiment, ring "A" is a six membered aromatic ring. In one embodiment ring "A" is a group Ω where Ω has the form:

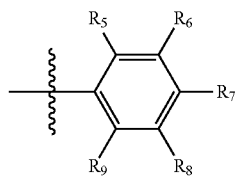

$R_5$-$R_9$ are independently selected from hydrogen, R, or $L_1$; and wherein any two adjacent groups $R_5$-$R_9$ (e.g., $R_5$ and $R_6$ or $R_6$ and $R_7$) may together form a five or six membered fused ring with ring "A," each optionally comprising from 1 to 6 (or from 1-4 or from 1-2) heteroatoms selected from oxygen, nitrogen, sulfur, and halogen (e.g., fluoro, chloro, bromo, iodo). In one embodiment, one or more (e.g., one, two, three, four, or five) of $R_5$-$R_9$ is —OH or —OR*. In one embodiment, two adjacent $R_5$-$R_9$ (e.g., $R_5$ and $R_6$ or $R_6$ and $R_7$) groups are —OH or —OR*. In one embodiment, two adjacent $R_5$-$R_9$ (e.g., $R_5$ and $R_6$ or $R_6$ and $R_7$) groups together form a group —O—$(CH_2)_q$—O—, wherein q is one or two. In one embodiment, $R_5$ and $R_6$ or $R_6$ and $R_7$ together form a group —O—$CH_2$—O—.

In another embodiment, $R_3$ is hydrogen or lower alkyl; and/or $R_4$ is a group of the form:

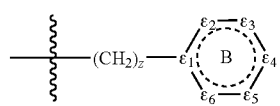

where "z" is an integer from 1-4; and ring "B" is a five or six-membered (optionally aromatic, or comprising zero, one, two, or three double bonds) ring, $\epsilon_1$ is C or N; and $\epsilon_2$-$\epsilon_6$ are independently selected from —N—, —NH—, —NR*—, —O—, —S—, —CH—, —CR—, —CR*—, and in the case where ring "A" is a five membered ring, $\epsilon_4$ is a bond (i.e., it is absent); and wherein $\epsilon_2$ or $\epsilon_6$ may also be a group —$NL_1$- or —$CL_1$-, where $L_1$ is a linking moiety that forms a linkage between ring "B" and $R_3$, where $L_1$ is group —$X^a$—$(CH_2)_n$—$(CH=CH)_m$—$X^b$—$(CH_2)_n$—$(CH=CH)_m$—$X^c$, where $X^a$, $X^b$, and $X^c$ are independently a bond (i.e., absent), —O—, —S—, —NH—, —NR*— and "n" and "m" are independently at each occurrence integers from 0-2, with the proviso that $L_1$ comprises no more than four (e.g., one, two, three, or four) atoms in the direct chain between ring "A" and $R_3$.

In one embodiment, "z" is an integer from 1-2, and/or ring B is a group Q (as defined above). In one embodiment, "z" is 1 and/or $R_3$ is hydrogen or methyl, and/or ring "B" is a group Q. In one embodiment, "z" is an integer from 1-2, and/or ring "B" is a group Ω. In another embodiment, "z" is 1, and/or $R_3$ is hydrogen or methyl, and/or ring B is a group Ω.

In one embodiment, one or more (e.g., one, two, three, four, or five) of $R_5$-$R_9$ is —OH or —OR*. In one embodiment, two adjacent $R_5$-$R_9$ (e.g., $R_5$ and $R_6$ or $R_6$ and $R_7$) groups are —OH or —OR*. In one embodiment, two adjacent $R_5$-$R_9$ (e.g., $R_5$ and $R_6$ or $R_6$ and $R_7$) groups together form a group —O—$(CH_2)_q$—O—, wherein q is one or two. In one embodiment, $R_5$ and $R_6$ or $R_6$ and $R_7$ together form a group —O—$CH_2$—O—.

In some embodiments, the cosmetic composition comprises a compound selected from the group consisting of:

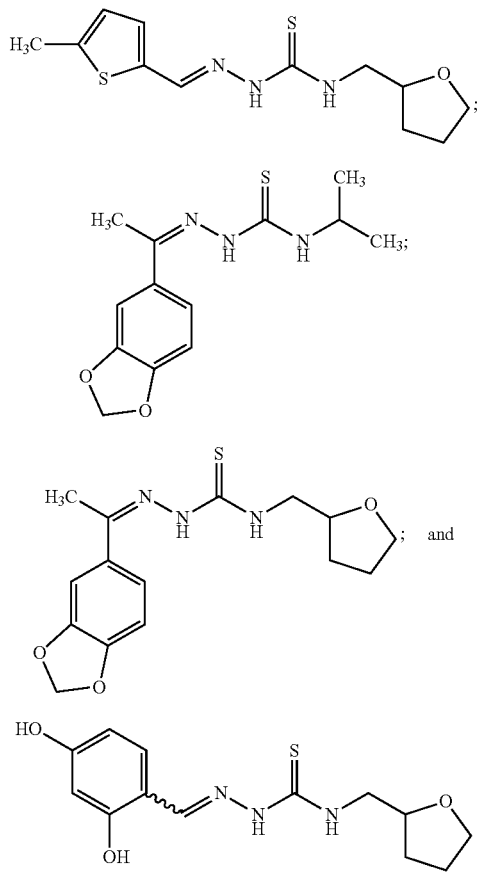

and cosmetically acceptable salts thereof.

In other embodiments, cosmetic composition may comprise a compound according to formula II(a):

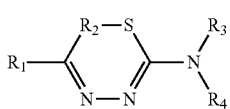

and cosmetically acceptable salts thereof. In one embodiment, $R_2$ is either a bond (i.e., it is absent) or a $C_{1-6}$ or $C_{1-3}$ aliphatic divalent radical. In some embodiments, $R_2$ is either a bond (i.e., it is absent) or a methylene group —$CH_2$—; and $R_1$, $R_3$, $R_4$, R and R* are as defined above (e.g., $R_1$, $R_3$, and $R_4$ may be, without limitation, hydrogen, lower alkyl, or five or six membered rings Q or Ω, etc.). An exemplary compound according to formula II(a) has the structure:

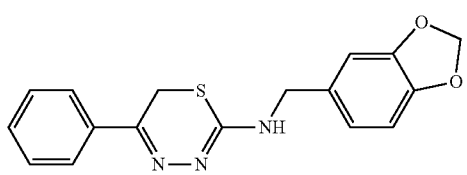

By "cosmetically acceptable" salts of the compounds of Formula I(a) and II(a) is meant salts that are safe for contact with a human integument. When the compounds are chiral, they may be racemic or may comprise and enantiomeric excess of either the R or S enantiomer at any stereocenter. Any double bonds may be in either the E or Z configuration.

The compounds of Formulas I(a) and II(a) may be formulated in cosmetically acceptable vehicles, which may comprises one or more of a film forming polymer, a thickener, a pH adjuster, a preservative, an emulsifier, a gelling agent, an antioxidant, a fragrance, a colorant, and the like. The vehicle may comprise a water-in-oil, oil-in-water, silicone-in-water, or water-in-silicone emulsion and will typically further comprise an emulsifier.

The effective amount of the compound of Formulas I(a) and II(a) will typically be from about 0.00001% to about 5%, more typically, from 0.0001% to about 2.5% by weight of the composition. In one embodiment the compound of Formulas I(a) and II(a) comprises from about 0.001% to about 1% by weight of the composition. In one embodiment the compound of Formulas I(a) and II(a) comprises from about 0.01% to about 0.1% by weight of the composition.

The compositions of the invention may be applied to human skin for depigmentation, including to reduce areas of unwanted pigmentation, such as hyperpigmentation, including age spots and freckles.

The compounds of Formulas I(a) and II(a) can be formulated in cosmetically acceptable vehicles (as described herein) and may include one or more additional agents that combat pigmentation or hyperpigmentation, including tyrosinase inhibitors and/or melanosome transfer inhibitors. Special mention may be made of thiodipropionic acid and esters thereof (notably, di-lauryl esters); hydroquinone and the monobenzyl ether thereof; hydroquinone-beta-D-glucopyranoside; retinoids (e.g., retinoic acid); tretinoin; azelaic acid; Kojic acid (5-hydroxy-4-pyran-4-one-2-methyl); Mequinol (4-hydroxyanisole); Niacinamide; soy protein and other serine protease inhibitors; paper mulberry extract; Glabridin (licorice extract); *Arctostaphylos patula* and *Arctostaphylos viscida* extracts; Magnesium-L-ascorbyl-2-phosphate (MAP); 4-Isopropylcatechol; Aleosin; N-acetyl-4-S-cysteaminylphenol and N-propionyl-4-S-cysteaminylphenol; N-acetyl glucosamine; and Tranexamic acid (trans-4-aminomethylcyclohexanecarboxylic acid); to name a few.

The compositions are applied topically to skin or topically applied to hair or other keratinous substrates. In certain embodiments, the cosmetic compositions described herein can be used to treat and/or prevent hyper-pigmentation of skin and/or that of the hair, for example, to lighten skin or hair. In some embodiments, the composition is topically applied to the skin or hair, for example to an area of hyper-pigmented skin or hair. Hyper-pigmentation includes any coloration of an individual's skin or hair that is darker than desired by the individual and that is caused by melanocytes. Such unwanted pigmentation may also be called discoloration. Hyper-pigmented areas of the skin include areas of discrete or mottled hyper-pigmentation. Areas of discrete hyper-pigmentation can be distinct, uniform areas of darker color and may appear as brown spots or freckles on the skin, including marks commonly called pigment spots or "age spots." Areas of mottled hyper-pigmentation of the skin can be dark blotches that are larger and more irregular in size and shape than areas of discrete pigmentation. Areas of hyper-pigmentation also include areas of tanned skin, e.g., skin tanned due to UV exposure. Hyper-pigmented hair includes any shade of hair that is darker than desired.

Skin hyper-pigmentation may be caused by any number of factors, including, for example, genetics, UV or sun exposure, age, scarring, or discoloration due to skin injury, including lacerations, burns, sunburn, acne, or other dermatological conditions, and the like. For example, skin hyper-pigmented areas include melasmic patches. Melasma is a common skin disorder involving facial skin discoloration, including one embodiment prevalent in pregnant women, where it is called chloasma faciei or chloasma. Melasmic (or chloasmic) patches may appear as dark brown, irregular patches on the face, on the upper cheeks, nose, lips, upper lip, and forehead. The patches often develop gradually over time and generally do not itch or otherwise hurt, but may negatively affect an individual's appearance. Skin hyper-pigmentation also refers to areas under the arm, e.g., that have become or are becoming darker than desired.

Skin hyper-pigmentation may or may not include areas under an individual's eyes that are darker than desired by the individual, commonly referred to as "under eye dark circles" or "dark circles." Dark circles are usually round, uniform areas of pigmentation beneath each eye, which may be caused by heredity, allergies, tiredness, or other causes. In one embodiment, the compositions are topically applied for the treatment of under eye dark circles. However, treatment of hyper-pigmentation, in some embodiments, excludes treating discoloration and/or bagginess in facial skin below the eyes because such pigmentation may entail an unrelated etiology to other hyperpigmentation conditions. Hyper-pigmented skin may also include skin in the axillary (i.e., underarm) region.

Treating hyper-pigmentation or hyper-pigmented skin/hair refers to eradicating, reducing, ameliorating, or reversing one or more of the unwanted features associated with hyper-pigmentation, such as producing a perceptible lightening of the skin or hair in the affected area. Lightening hyper-pigmented areas of the skin may be desirable, in one embodiment, in diminishing age spots; lightening a suntan; evening or optimizing skin tones, e.g., in areas of mottled hyper-pigmentation; in treating melasmic and chloasmic patches, freckles, after-burn scars, and post-injury hyper-pigmentation. Preventing hyper-pigmentation or hyper-pigmented skin refers to affording skin, not yet affected by hyper-pigmentation, a benefit that serves to avoid, delay, forestall, or minimize one or more unwanted features associated with skin hyper-pigmentation, such as reducing the darkness or size of hyper-pigmented areas that eventually develop.

The inventive compositions are capable of treating and/or preventing hyper-pigmented skin and can be referred to as "skin lighteners." When used for lightening hair, they can be referred to "hair lighteners." In one embodiment, the compositions of the present invention are usable to lighten hair in a non-bleaching manner; that is, by suppressing the formation and/or transportation of melanin out of follicular melanocytes, rather than by bleaching the hair itself. In one embodiment, the hair lightened by the instant invention includes facial hair (e.g., hair above the upper lip) and body hair (e.g., arms and legs), as opposed to scalp hair. In one embodiment, the hair lightener is applied to facial hair located on the upper lip.

The compositions are applied to the skin for a period of time sufficient to diminish the appearance of melanin in the skin. The compositions may be applied topically once, twice, or more daily. The treatment may be for a period of one week, two weeks, four weeks, eight weeks, or more. In one embodiment, the compositions of the invention will be applied to the skin in an amount from about 0.001 to about 100 mg/cm$^2$, more typically from about 0.01 to about 20 mg/cm$^2$, or from about 0.1 to about 10 mg/cm$^2$.

The cosmetic compositions of this invention may further comprise a retinoid. Retinoids may be without limitation retinol (Vitamin A) and esters thereof, such as retinol palmitate, retinol acetate and retinol propionate, and salts thereof, retinaldehyde, or retinoic acid (e.g., all-trans or 13-cis) and derivatives thereof. The cosmetic compositions of this invention may further comprise alpha-hydroxy acids, such as glycolic acid, or beta hydroxyl acids, such as salicylic acid.

In practice, the compositions of the invention may be applied, alone or in cosmetically acceptable vehicles, to skin in need of treatment. That is, skin which suffers from a deficiency or loss in any of the foregoing attributes (including skin in need of depigmentation) or which would otherwise benefit from improvement in any of the foregoing skin attributes.

The compositions may be applied directly to the skin or to a particular area of skin in need of depigmentation such as directly to an age spot or sun spot or dark circle on the skin of the face, neck, lips, chest, arms, legs, and/or hands.

The cosmetic compositions according to the invention can be formulated in a variety of forms for topical application and will comprise from about 0.00001% to about 90% by weight of a compound of Formulas I(a) and II(a), and typically will comprise such actives in an amount from about 0.0001% to about 25% by weight, and more typically from about 0.001% to about 10% by weight. In some embodiments, the compounds of Formulas I(a) and II(a) will individually or collectively comprise from 0.01% to about 5% by weight of the composition. When the cosmetic compositions according to the invention are formulated in a liquid form, they typically will be present at a concentration from about 0.001 μM to about 50 μM, or from about 0.5 μM to about 10 μM, or from about 2.25 μM to about 10 μM.

The compositions can include a cosmetically acceptable vehicle. Such vehicles may take the form of any known in the art suitable for application to skin and may include, but are not limited to, water; vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, hydrocarbon oils such as mineral oil, petrolatum, isoeicosane and polyisobutene; polyols such as propylene glycol, glycerin, butylene glycol, pentylene glycol and hexylene glycol; liposomes; waxes; or any combinations or mixtures of the foregoing.

The vehicle may comprise an aqueous phase, an oil phase, an alcohol, a silicone phase or mixtures thereof and may be in the form of an emulsion. Non-limiting examples of suitable emulsions include water-in-oil emulsions, oil-in-water emulsions, silicone-in-water emulsions, water-in-silicone emulsions, glycerin-in-oil emulsions, wax-in-water emulsions, water-oil-water triple emulsions or the like. The emulsion may include an emulsifier, such as a nonionic, anionic or amphoteric surfactant, or a gelling agent.

In one embodiment, the topical composition will have a pH range from 1 to 8, with a pH in the range of from 2 to 7 being typical. In some embodiments, the composition will have a pH in the range of from 3.5 to 5.5. Suitable pH adjusters such as citric acid and triethanolamine may be added to bring the pH within the desired range.

In one embodiment of the invention, the compositions may include additional skin actives, including but not limited to, retinoids, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors.

The composition may comprise additional active ingredients having anti-aging benefits, as it is contemplated that synergistic improvements may be obtained with such combinations. Exemplary anti-aging components include, without limitation, botanicals (e.g., *Butea frondosa* extract); phytol; thiodipropionic acid (TDPA) and esters thereof; retinoids (e.g., 9-cis retinoic acid, 13-cis retinoic acid, all-trans retinoic acid and derivatives thereof, phytanic acid, retinol (Vitamin A) and esters thereof, such as retinol palmitate, retinol acetate and retinol propionate, and salts thereof and others); hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few.

Exemplary retinoids include, without limitation, retinoic acid (e.g., all-trans or 13-cis), and derivatives thereof, retinaldehyde, retinol (Vitamin A) and esters thereof, such as retinol palmitate, retinol acetate and retinol propionate, and salts thereof. Particular mention may be made of retinol. It is contemplated that combinations of the compounds of Formulas I(a) and II(a) with any of these retinoids will provide enhanced or synergistic improvements to skin. The retinoids will typically be included in amounts from about 0.0001% to about 5% by weight, more typically from about 0.01% to about 2.5% by weight, or from about 0.1% to about 1.0% by weight. Compositions according to this embodiment will typically include an antioxidant such as ascorbic acid and/or BHT and/or a chelating agent such as EDTA or a salt thereof.

In another embodiment, the topical compositions of the present invention may also include one or more of the following: a skin penetration enhancer; an emollient, such as isopropyl myristate, petrolatum, volatile or non-volatile silicones oils (e.g., methicone, dimethicone), ester oils, mineral oils, and fatty acid esters; a humectant, such as glycerin, hexylene glycol or caprylyl glycol; a skin plumper, such as palmitoyl oligopeptide, collagen, collagen and/or glycosaminoglycan (GAG) enhancing agents; a sunscreen, such as avobenzone; an exfoliating agent; and an antioxidant.

Suitable exfoliating agents include, for example, alpha-hydroxy acids, beta-hydroxy acids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. One exemplary exfoliating agent is glycolic acid. When present, the exfoliating agent may comprise from about 0.01% to about 20% by weight of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. In one particular embodiment, the inventive compositions will include TDPA or an ester thereof (e.g., dilauryl thiodipropionic acid), and/or an alpha hydroxyl acid (glycolic acid) and/or beta hydroxyl acid (salicylic acid or a derivative). Compositions of the present invention may comprise an antioxidant, which may comprise from about 0.001 wt % to about 10 wt %, or from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents; metal chelating agents such as EDTA or salts thereof; pigments; colorants; and pH adjusters. The composition may optionally comprise other components known to those skilled in the art including, but not limited to, film formers, moisturizers, minerals, viscosity and/or rheology modifiers, anti-acne agents, insect repellents, skin cooling compounds, skin protectants, lubricants, fragrances, preservatives, stabilizers, and mixtures thereof. In addition to the foregoing, the cosmetic compositions of the invention may contain any other compound for the treatment of skin disorders. The conventional additives, actives, adjuvants, and excipients set forth in the preceding paragraphs are present in the compositions in amounts suitable to obtain their intended purpose and effect, each typically being present in an amount of from 0.01 to 25% by weight of the cosmetic composition, in particular from about 0.1 to 5% by weight of the cosmetic composition.

The composition may be formulated in a variety of product forms, such as, for example, an emulsion, lotion, cream, serum, spray, aerosol, cake, ointment, essence, gel, paste, patch, pencil, towelette, mask, stick, foam, elixir, concentrate, and the like, particularly for topical administration. The composition is typically formulated as an emulsion, lotion, cream, ointment, serum or gel.

In another aspect of the invention, the compositions are applied topically to improve the aesthetic appearance of human skin. The method comprises topically applying to an area of the skin in need thereof a composition comprising an effective amount of a compound of Formulas I(a) and II(a), for a time sufficient to improve the aesthetic appearance of said human skin. The compositions are topically applied to the skin in effective amounts, by which is meant an amount sufficient to achieve a measurable improvement in skin health or reduction in one or more dermatological signs of aging with daily (once, twice, etc.) administration, typically for a period of at least one week or more.

The aesthetic improvement of human skin may be an improvement of any attribute or characteristic of skin, including without limitation:

(a) treatment, reduction, and/or prevention of fine lines or wrinkles;

(b) reduction of skin pore size;

(c) improvement in skin thickness, plumpness, and/or tautness;

(d) improvement in skin smoothness, suppleness and/or softness;

(e) improvement in skin tone, radiance, and/or clarity;

(f) improvement in procollagen, and/or collagen production;

(g) improvement in maintenance and remodeling of elastin;

(h) improvement in skin texture and/or promotion of retexturization;

(i) improvement in skin barrier repair and/or function;

(j) improvement in appearance of skin contours;

(k) restoration of skin luster and/or brightness;

(l) replenishment of essential nutrients and/or constituents in the skin;

(m) improvement of skin appearance decreased by aging and/or menopause;

(n) improvement in skin moisturization;

(o) increase in skin elasticity and/or resiliency;

(p) treatment, reduction, and/or prevention of skin sagging;

(q) improvement in skin firmness; and (r) reduction of pigment spots and/or mottled skin; and (s) improvement of optical properties of skin by light diffraction or reflection.

In a related implementation, a method is provided for the treatment of wrinkles and/or fine lines on the skin human skin (typically, skin of the face) comprising topically applying to an area of the skin in need thereof (e.g., applying to a wrinkle or fine line) a composition of Formulas I(a) and II(a), for a time sufficient to improve the aesthetic appearance of said human skin. The treatment may be a least once or twice daily and may last for a period of at least four weeks, typically at least eight weeks or longer. The composition may optionally further comprise a retinoid (e.g., retinol or retinyl palmitate) and/or an alpha-hydroxy acid (e.g., glycolic acid) and/or a beta-hydroxy acid (e.g., salicylic acid or derivative) in amounts effective to improve the appearance of skin.

In a related aspect, methods are provided for enhancing the production of collagen or pro-collagen in human skin comprising topically applying to an area of the skin in need thereof (e.g., sagging skin, thinning skin, skin suffering from wrinkles and fine lines, etc.) a topical composition comprising a cosmetically acceptable vehicle, and an effective amount of a compound of Formulas I(a) and II(a), for a time sufficient to improve the appearance thereof. The treatment may be a least once or twice daily and may last for a period of at least four weeks, typically at least eight weeks or longer. The composition may optionally further comprise a retinoid and/or an alpha-hydroxy acid (e.g., glycolic acid) and/or a beta-hydroxy acid (e.g., salicylic acid or a derivative) in amounts effective to improve the appearance of skin.

In yet another aspect of the invention, methods are provided for reducing the severity of, reducing the number of, or preventing or forestalling the onset of, wrinkles or fine lines on human skin comprising topically applying to an area of the skin in need thereof (e.g., wrinkled skin), an effective amount (e.g., 0.0001%-1% by weight, w/w) of a compound of Formulas I(a) and II(a), in combination with an effective amount (e.g., 0.01%-5% by weight, w/w) of retinol and/or an effective amount (e.g., 0.001%-5% by weight, w/w) of an alpha-hydroxy acid (e.g., glycolic acid) and/or a beta-hydroxy acid (e.g., salicylic acid).

The invention provides a method for treating aging skin by topically applying a composition comprising a collagen-stimulating compound of Formulas I(a) and II(a), typically in a cosmetically acceptable vehicle, over the affected area for a period of time sufficient to remediate, reverse, reduce, ameliorate, or prevent dermatological signs of aging. Generally, the improvement in the condition and/or aesthetic appearance is selected from the group consisting of: reducing dermatological signs of chronological aging, photoaging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation or hypopigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; slowing or halting skin thinning; increasing skin elasticity and/or resiliency; enhancing exfoliation; improving microcirculation; decreasing and/or preventing cellulite formation; and any combinations thereof. In some embodiments, each of the forgoing is associated with female skin.

In some embodiments, the compounds of Formulas I(a) and II(a) will be used to reduce the severity of fine lines or wrinkles, often in combination with retinol. The composition will typically be applied to the skin one, two, or three times daily for as long as is necessary to achieve desired results. The treatment regimen may comprise daily application for at least one week, at least two weeks, at least four weeks, at least eight weeks, or at least twelve weeks or more. Chronic treatment regimens are also contemplated. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). In one embodiment, the cosmetic compositions of the invention will be applied to the skin in an amount from about 0.001 to about 100 mg/cm$^2$, more typically from about 0.01 to about 20 mg/cm$^2$, or from about 0.1 to about 10 mg/cm$^2$.

It is also contemplated that the compositions of the invention will be useful for treating thin skin by topically applying the composition to thin skin of an individual in need thereof. "Thin skin" is intended to include skin that is thinned due to chronological aging, menopause, or photodamage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in individuals that have not manifested signs of skin aging, most commonly in individuals under 25 years of age. The method may also reverse or treat signs of aging once manifested as is common in individuals over 25 years of age, or to slow the progression of dermatological aging in such individuals.

In one embodiment, the compositions of the invention are applied to human skin to reduce sebum production or improve the appearance of skin affected by cellulite, and/or reduce unwanted lipogenesis or increase lipolysis. In this embodiment, the compounds of Formulas I(a) and II(a) can be formulated in cosmetically acceptable vehicles (as described herein) and may include one or more additional agents such as anti-acne ingredients (e.g., salicylic acid, benzoyl peroxide and other peroxides, sulfur, retinoids, etc.) in the case of a facial composition, or, in the case of a cellulite treatment, the formulation may comprise any ingredients suitable for treatment of cellulite, including without limitation, perilla oil and other unsaturated fatty oils and omega-3 fatty acids such as alpha-linolenic acid; caffeine; theophylline; xanthines; retinoids (e.g., retinol); and the like. A cellulite treatment according to the invention will typically be applied topically to skin suffering from cellulite, including skin of the buttocks and thighs for a period of time sufficient to improve the appearance thereof, including for example, daily treatment for at least four weeks, at least eight weeks, at least twelve weeks, or longer. In one embodiment, the compositions are topically applied to treat acne.

In another embodiment, the compounds of Formulas I(a) and II(a) are intended for oral use, including for pharmaceutical use. Pharmaceutical formulations will include pharmaceutically acceptable carriers (i.e., diluents and excipients). The pharmaceutical compositions may be included in solid dosage forms, including compressed tablets and capsules, or in liquid or powder forms. Pharmaceutical dosage forms will typically include from about 0.5 mg to about 200 mg, or from about 1 mg to about 100 mg of the compound of Formulas I(a) and II(a). The dosage forms may be immediate release, in which case they will typically comprise a water-soluble or dispersible carrier such as microcrystalline cellulose, mannitol, hydroxypropyl methyl cellulose, PVP or the like, or may be delayed, sustained, or modified release, in which case they may comprise water-insoluble polymers such as cellulose ethers (e.g., ethylcellulose), alone or in combination with water soluble or dispersible polymers, to regulate the rate of dissolution of the dosage form in the stomach.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, §201(i).

EXAMPLES

The following example describes specific aspects of the invention to illustrate the invention but should not be construed as limiting the invention, as the example merely provide specific methodology useful in the understanding and practice of the invention and its various aspects.

Example 1

Mushroom Tyrosinase Assay.

Mushroom tyrosinase and L-Tyrosine were obtained from Sigma-Aldrich, Inc. (St. Louis, Mo.). The enzyme activity was measured in buffer containing 100 mM phosphate buffer pH 6.8, 5% absolute ethanol, 2 micrograms/milliliter mushroom tyrosinase, and 0.2 mg/ml L-Tyrosine. The reaction (conversion of L-Tyrosine to DOPAchrome) was conducted in triplicates at 25° C. for 30 min, and absorbance was then measured at 492 nm. Kojic Acid was used as a positive control inhibitor in these assays. Percent change in tyrosinase activity relative to vehicle control was calculated. Table 1 shows the effect of treatment with each substance on tyrosinase synthesis in the mushroom tyrosinase assay.

TABLE 1

PERCENT CHANGE IN TYROSINASE ACTIVITY COMPARED TO DMSO VEHICLE CONTROL MUSHROOM TYROSINASE ASSAY

| Test Compound | Concentration | Tyrosinase Inhibition |
| --- | --- | --- |
| AV6989 | 0.001% | −36% |
| AV6989 | 0.01% | −75% |

Example 2

Inhibition of Melanin Production.

The effects of various test compounds on melanin levels were determined by performing assays using B16 melanoma cells. These cells are known to constitutively produce melanin and are a commonly utilized and accepted model system for monitoring the inhibition of melanin synthesis. The B16 mouse melanoma cells were seeded (ATCC, cat. #: CRL-6475) into 96-well tissue culture-treated plates (BD Falcon) and treated with test actives or controls in phenol red free DMEM (Mediatech; cat. #: 17-205-CV) with 2 nanogram/ml of alpha MSH (Fluka; cat #: 63605). The cells were examined for their ability to modulate pigment formation. Cells were exposed to diluted test actives or control, where test active had a final concentration of 0.001% or 0.0001%. Tests were performed in 6 replicates each. Following the treatment period (4 days), the level of pigment produced or melanin synthesized was quantified by reading the absorbance at 540 nm using a standard microplate reader (Tecan Group Ltd.).

After quantifying the amount of melanin, cell viability was determined using the MTT conversion method. The MTT conversion method measures the reduction of the MTT dye from a yellow colored, water-soluble, tetrazolium salt to a bluish-purple colored insoluble formazan precipitate by NAD(P)H-dependent microsomal dehydrogenase enzymes, which only function in viable cells. The intensity of the blue color is indicative of cell viability. After quantifying the amount of melanin pigment produced, the cells were exposed to MTT dye solution (1 mg/ml) for two to three hours. Formazan material was solubilized with reagent alcohol (95% ethanol: 5% isopropanol) and shaken on an orbital shaker for 15-30 minutes. MTT dye uptake and conversion by viable cells were determined by measuring the extracted formazan at 570 nm using a microplate reader. Total pigmentation was calculated, normalized to cell viability values and expressed as the average percent change in melanin activity relative to control of the six experiments performed.

Table 2 shows the effect of treatment with each substance on melanin levels using a B16 melanoma cell assay.

TABLE 2

PERCENT CHANGE IN MELANIN COMPARED TO DMSO VEHICLE CONTROL IN B16 CELL ASSAY

| Test Compound | Concentration | B16 Assay Pigmentation Decrease |
|---|---|---|
| AV6989 | 0.0001% | −79% |
| AV1221 | 0.0001% | ++ |
| AV1221 | 0.001% | ++++ |
| AV3715 | 0.0001% | + |
| AV3715 | 0.001% | ++++ |
| AV3793 | 0.0001 | + |
| AV3793 | 0.001 | +++ |
| AV2043 | 0.0001 | ++ |

The assay data in Table 2 uses the following scale: 0: <10% decrease; +: between 20-30% decrease; ++: 31-50% decrease; +++: between 51-70% decrease; ++++: >71% decrease; C=cytotoxic Example 3

Inhibition of Melanin Production in Human Primary Melanocyte

The effects of various test compounds on melanin productions were determined by performing assays using Human Epidermal Melanocytes, neonatal, darkly pigmented donor (HEMn-DP). The HEMn-DP cells were seeded (Invitrogen; cat. #: C-202-5C) into 6-well tissue culture-treated plates (BD Falcon) and treated with test actives or controls in Medium 254 (Invitrogen; cat. #: M-254-500) supplemented with 1% HMSG (Invitrogen; cat. #: S-002-5) and 1% P/S. The cells were examined for their ability to modulate pigment formation. Cells were exposed to diluted test actives or control, where test active had a final concentration of 0.001% or 0.0001%. Tests were performed in triplicates each. Following the treatment period (5 days), supernatants were aspirated. The melanin was extracted with 0.5 ml of 2N NaOH for 30 minutes at 80° C. The level of melanin synthesized within the cells was quantified by reading the absorbance at 405 nm using a standard microplate reader (Tecan Group Ltd.).

The cell viability was determined using the MTT conversion method. The MTT conversion method measures the reduction of the MTT dye from a yellow colored, water-soluble, tetrazolium salt to a bluish-purple colored insoluble formazan precipitate by NAD(P)H-dependent microsomal dehydrogenase enzymes, which only function in viable cells. The intensity of the blue color is indicative of cell viability. The cells were exposed to diluted test actives or control, where test active had a final concentration of 0.001% or 0.0001% for 6 days. The cells were then exposed to MTT dye solution (1 mg/ml) for two to three hours. Formazan material was solubilized with reagent alcohol (95% ethanol: 5% isopropanol) and shaken on an orbital shaker for 15-30 minutes. MTT dye uptake and conversion by viable cells were determined by measuring the extracted formazan at 570 nm using a microplate reader. Total pigmentation was calculated and normalized to cell viability values. The average percent change in melanin relative to control of the triplicates from the Human Primary Melanocyte Pigmentation Assay (HEMn-DP Pigmentation) is reported in the Table 3 in accordance with the scale: 0: <10% decrease in pigmentation level; +: between 11-30% decrease; ++: between 31-50% decrease; +++: between 51-70% decrease; ++++: >71% decrease; C=cytotoxic.

TABLE 3

CHANGE IN MELANIN COMPARED TO DMSO VEHICLE CONTROL IN HUMAN PRIMARY MELANOCYTE PIGMENTATION ASSAY

| Test Compound | Concentration | HUMAN PRIMARY MELANOCYTE PIGMENTATION ASSAY |
|---|---|---|
| AV1221 | 0.0001% | + |
| AV1221 | 0.001% | ++++ |
| AV3715 | 0.0001% | 0 |
| AV3715 | 0.001% | + |
| AV3793 | 0.0001 | 0 |
| AV3793 | 0.001 | +++ |
| AV2043 | 0.0001 | + |
| AV2043 | 0.001 | ++ |

Example 4

Inhibition of Melanin Production in 3D Skin Equivalent Tissue

The effect of the tyrosinase inhibitors on melanin levels was investigated using a MELANODERM™ (MEL-300-B, MatTek Corp., Ashland, Mass.) human skin model. MEL-ANODERM™ is a viable reconstituted three-dimensional human skin equivalent containing melanocytes derived from African-American donors. Tissues were maintained in culture medium EPI-100-NMM-113 at 37° C. as recommended by the manufacturer.

The compounds were dissolved in either 69% propylene glycol+30% EtOH+1% DMSO or 70% propylene glycol+30% EtOH to the final concentrations of either 0.1%, 0.25%, or 0.5% (w/v). 10 μl of the solution was applied topically to the MELANODERM™ tissue while culture medium was added on days 1, 2, 4, 7, and 9. Control tissues were treated with the 10 μl of corresponding vehicle only. On Day 11, tissues were collected and homogenized in a buffer containing 1% SDS, 50 mM EDTA, and 10 mM Tris, pH 6.8. To each homogenate, protease K (5 mg/ml) was added and incubated overnight at 45° C. Additional protease K was added and incubated for 4 hours at 45° C., followed by the addition of 0.5M sodium carbonate and 30% $H_2O_2$ and incubation at 80° C. for 30 minutes. The samples were cooled down to room temperature, and extracted with chloroform/methanol (2:1). After centrifugation at 10,000 g for 10 minutes, absorbance of the top phase was measured at 450 nm. Percent change in melanin levels in treated tissue was calculated relative to control. The average percent change in melanin relative to control of the three tissues is reported in the Table 4 in accordance with the scale: 0: <7% decrease in pigmentation level; +: between 8-14% decrease; ++: between 15-20% decrease; +++: between 21-30% decrease; ++++: >31% decrease; C=cytotoxic

TABLE 4

CHANGE IN MELANIN COMPARED TO DMSO VEHICLE CONTROL IN 3D SKIN EQUIVALENT TISSUE PIGMENTATION ASSAY

| Test Compound | Concentration | 3D Tissue Pigmentation Assay |
| --- | --- | --- |
| AV1221 | 0.05% | +++ |
| AV1221 | 0.1% | ++ |
| AV3715 | 0.05% | + |
| AV3715 | 0.1% | ++ |
| AV3793 | 0.05% | ++ |
| AV3793 | 0.1% | +++ |
| AV2043 | 0.05% | +++ |
| AV2043 | 0.1% | +++ |

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A topical composition comprising a cosmetically acceptable vehicle and a compound selected from the group consisting of:

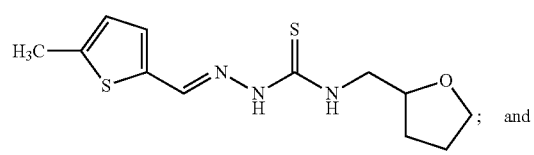
AV3793

; and

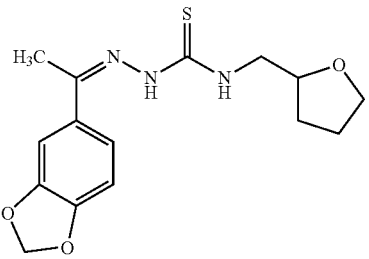
AV1221 or cosmetically acceptable salts thereof.

2. A topical composition comprising a cosmetically acceptable vehicle and a compound having the structure:

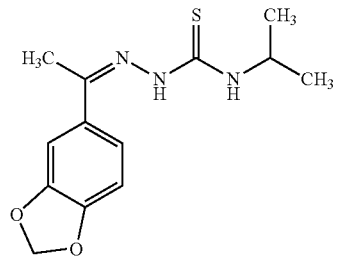
AV2043 or cosmetically acceptable salts thereof.

3. The topical composition according to claim 2, further comprising a cosmetic ingredient selected from a film forming polymer, a thickener, a pH adjuster, a preservative, an emulsifier, a gelling agent, an antioxidant, an emollient, a humectant, a fragrance, or a colorant.

4. The topical composition according to claim 1, further comprising a cosmetic ingredient selected from a film forming polymer, a thickener, a pH adjuster, a preservative, an emulsifier, a gelling agent, an antioxidant, an emollient, a humectant, a fragrance, or a colorant.

5. The topical composition according to claim 1, wherein said compound is present in an amount from about 0.001 to about 10% by weight of said topical composition.

6. The topical composition according to claim 2, wherein said compound is present in an amount from about 0.001 to about 10% by weight of said topical composition.

7. The topical composition according to claim 1, wherein said cosmetically acceptable vehicle is in the form of an emulsion comprising and emulsifier.

8. The topical composition according to claim 2, wherein said cosmetically acceptable vehicle is in the form of an emulsion comprising and emulsifier.

* * * * *